United States Patent [19]

Merger et al.

[11] Patent Number: 4,672,137
[45] Date of Patent: Jun. 9, 1987

[54] PREPARATION OF 1,3-DI(ALKOXYCARBONYLAMINO)PROPANES

[75] Inventors: Franz Merger; Joerg Liebe, both of Frankenthal, Fed. Rep. of Germany

[73] Assignee: BASF Aktiengesellschaft, Ludwigshafen, Fed. Rep. of Germany

[21] Appl. No.: 856,971

[22] Filed: Apr. 29, 1986

[30] Foreign Application Priority Data

May 11, 1985 [DE] Fed. Rep. of Germany ....... 3517110

[51] Int. Cl.⁴ ............... C07C 125/07; C07C 125/073; C07C 125/075
[52] U.S. Cl. ..................................... 560/25; 560/115; 560/158
[58] Field of Search ........................ 560/25, 115, 158

[56] References Cited

U.S. PATENT DOCUMENTS 3,277,098 10/1966 Mexten ................................. 560/25

FOREIGN PATENT DOCUMENTS 1158492 6/1964 Fed. Rep. of Germany .

OTHER PUBLICATIONS

Chem. Rev. 65 583 (1965).
Houben-Weyl, 4th ed., vol. VIII, p. 138.

*Primary Examiner*—Bernard Helfin
*Attorney, Agent, or Firm*—Keil & Weinkauf

[57] ABSTRACT

1,3-Di(alkoxycarbonylamino)propanes of the general formula I

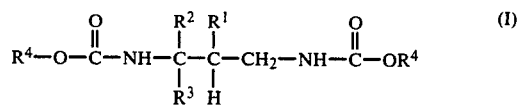

where $R^1$, $R^2$ and $R^3$ can be identical or different and each is hydrogen, or an aliphatic, cycloaliphatic, araliphatic or aromatic radical, and $R^4$ is an aliphatic, cycloaliphatic or araliphatic radical, are prepared by reacting an α,β-unsaturated aldehyde with a carbamic acid ester by reacting in a first stage as the α,β-unsaturated aldehyde a compound of the general formula II

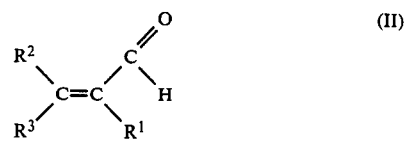

where $R^1$, $R^2$ and $R^3$ have the abovementioned meanings, with a carbamic acid ester of the general formula III

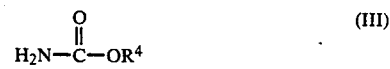

where $R^4$ has the abovementioned meanings, at 0°–150° C. to give a 1,1,3-tri(alkoxycarbonylamino)propane of the general formua IV

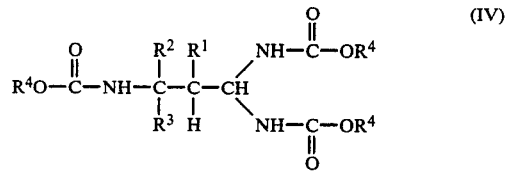

where $R^1$, $R^2$, $R^3$ and $R^4$ have the abovementioned meanings, and in a second stage heating the compound of the general formula (IV) in the presence of a hydrogenation catalyst and hydrogen under 1–300 bar at 100°–300° C.

6 Claims, No Drawings

PREPARATION OF 1,3-DI(ALKOXYCARBONYLAMINO)PROPANES

The present invention relates to a process for preparing unsubstituted or substituted 1,3-di(alkoxycarbonylamino)-propanes by reacting $\alpha,\beta$-unsaturated aldehydes with N-unsubstituted carbamic acid esters in the presence of acid catalysts to give 1,1,3-tri(alkoxycarbonylamino)propanes and hydrogenolytically cleaving the latter at elevated temperature and pressure in the presence of hydrogenation catalysts.

Substituted 1,3-di(alkoxycarbonylamino)propanes (propane-1,3-diurethanes) can be processed to propane-1,3-diamines and on the other hand are important starting materials for preparing active substances or precursors thereof, for example 2-oxohexahydropyrimidines. 1,3-Di(alkoxycarbonylamino)propanes can also be thermally cleaved to give 1,3-diisocyanates, which can be used as monomers of high isocyanate number for preparing polyurethanes.

The reaction of N-unsubstituted carbamic acid esters with $\alpha,\beta$-unsaturated aldehydes to form 1,1,3-tri(alkoxycarbonylamino)propanes is described in Chem. Rev. 65 (1965), 583. In the reactions described, the yields range from 20 to 40% and the catalyst used was hydrochloric acid. Two further publications, Glasnik Hemijskog Drustva, Beograd, 34 (1969), 387 to 394 and ibid 41 (1976), 219 to 224, describe the synthesis of some specific 1,1,3-tri(alkoxycarbonylamino)propanes. The catalysts used there are again hydrochloric acid as well as hydrogen chloride and boron trifluoride etherate, i.e. very corrosive reagents. In the workup, it is necessary to wash with water to remove the acid. The yields of triurethanes, apart from one specific exception (80%) range from 20 to 50%.

Substituted 1,3-di(alkoxycarbonylamino)propanes can be prepared by reacting 1,3-diaminopropanes with chloroformic acid esters; cf. Houben-Weyl, 4th edition, Volume VIII, page 138. This method has the disadvantage that difficult to obtain starting materials, such as the 1,3-diaminopropane compounds, are required. In addition, the reaction produces sizeable amounts of hydrogen chloride as a by-product.

DE-A-1,158,492 describes the reaction of 1,1-alkylidene diurethanes with cationically polymerizable mono- and/or polyolefins. This method always gives rise to mixtures of the desired 1,3-diurethane with 1,5- and higher diurethanes.

It is an object of the present invention to provide a process of the type mentioned at the beginning, which permits the preparation of 1,3-di(alkoxycarbonylamino)propanes in high purity and without using chlorine-containing starting compounds.

We have found that this object is achieved with a process for preparing 1,3-di(alkoxycarbonylamino)propanes of the general formula I

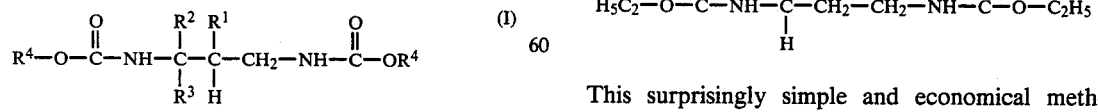

where $R^1$, $R^2$ and $R^3$ can be identical or different and each is hydrogen or an aliphatic, cycloaliphatic, araliphatic or aromatic radical and $R^4$ is an aliphatic, cycloaliphatic or araliphatic radical, by reacting an $\alpha,\beta$-unsaturated aldehyde with a carbamic acid ester, which comprises reacting in a first stage as the $\alpha,\beta$-unsaturated aldehyde a compound of the general formula II

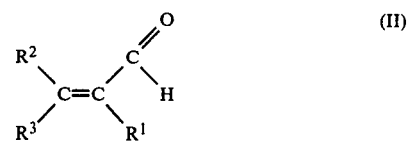

where $R^1$, $R^2$ and $R^3$ have the abovementioned meanings, with a carbamic acid ester of the general formula III

where $R^4$ has the abovementioned meanings, at 0°–150° C. to give a 1,1,3-tri(alkoxycarbonylamino)propane of the general formula IV

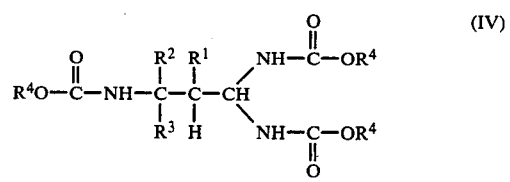

where $R^1$, $R^2$, $R^3$ and $R^4$ have the abovementioned meanings, and in a second stage heating the compound of the general formula (IV) in the presence of a hydrogenation catalyst and hydrogen under 1–300 bar at 100°–300° C.

The reaction can be represented for the case of using crotonaldehyde and ethyl carbamate by the following formulae

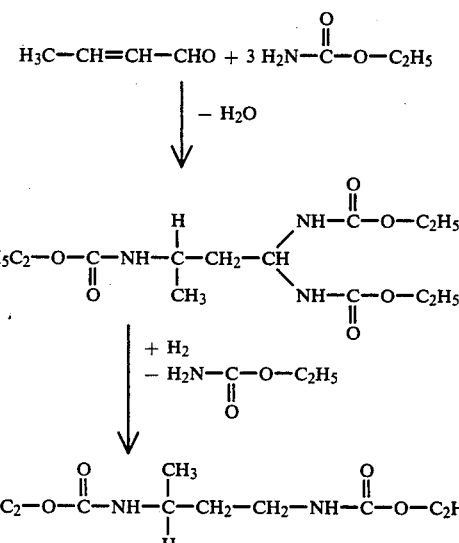

This surprisingly simple and economical method gives substituted 1,3-di(alkoxycarbonylamino)propanes from readily obtainable starting materials without using chlorine-containing reagents and hence without obtaining chlorine-containing by-products. A further advantage of this process is the high purity of the resulting products.

Preference is given to using starting materials of the general formulae II and III in which the radicals $R^1$, $R^2$ and $R^3$ can be identical or different and each be alkyl of from 1 to 30, in particular from 1 to 12, carbon atoms, cycloalkyl, aralkyl of from 7 to 12 carbon atoms, phenyl or hydrogen. The abovementioned radicals can in addition be substituted by groups which are inert under the reaction conditions, in particular by alkyl or alkoxy, of in each case from 1 to 4 carbon atoms. $R^4$ in the general formula III is preferably alkyl of from 1 to 12 carbon atoms, cycloalkyl or aralkyl of from 7 to 12 carbon atoms. These radicals can in addition be substituted by groups which are inert under the reaction conditions, in particular alkyl or alkoxy, each of from 1 to 4 carbon atoms. The corresponding intermediates of the general formula IV and the end products of the general formula I are particularly preferred products.

Suitable starting materials of the general formula II are for example: acrolein, methacrolein, ethylacrolein and higher homologs, crotonaldehyde, 2-methylpentenal, tiglinaldehyde, cinnamaldehyde and 2-benzylacrolein. Suitable starting materials of the general formula III are for example: methyl carbamate, ethyl carbamate, propyl carbamate, isopropyl carbamate, butyl carbamate, isobutyl carbamate sec-butyl carbamate, pentyl carbamate, 3-methylbutyl carbamate, hexyl carbamate, 2-ethylhexyl carbamate, heptyl carbamate, octyl carbamate, nonyl carbamate, decyl carbamate, undecyl carbamate, dodecyl carbamate, cyclohexyl carbamate, cyclopentyl carbamate, benzyl carbamate and methoxyethyl carbamate.

The N-unsubstituted aliphatic carbamates of the formula III can be prepared from urea and the corresponding alcohol without using phosgene. Preference is given to methyl carbamate, ethyl carbamate, propyl carbamate, n-butyl carbamate and i-butyl carbamate.

The reaction of the 1st stage, namely the preparation of the intermediate of the general formula IV, is carried out at 0°–150° C., preferably 20°–120° C., in particular 50°–90° C., under atmospheric or superatmospheric pressure, batchwise or continuously. If superatmospheric pressure is employed, values of from 1 to 10 bar are particularly favorable. It is advantageous to carry out the reaction in a solvent which is inert under the reaction conditions, but the use of a solvent is not mandatory. Suitable solvents are: aromatic hydrocarbons, e.g. benzene, toluene, ethylbenzene, o-, m-, p-xylene, isopropylbenzene; halohydrocarbons, in particular chlorohydrocarbons, e.g. methylene chloride, chloroform, carbon tetrachloride, tetrachloroethylene, 1,1,2,2- or 1,1,1,2-tetrachloroethane, amyl chloride, dichloropropane, dichlorobutane, 1,1,1- or 1,1,2-trichloroethane, trichloroethylene, pentachloroethane, 1,2-dichloroethane, 1,1-dichloroethane, n-propyl chloride, 1,2-cis-dichloroethylene, chlorobenzene, o-, m-, p-dichlorobenzene, o-, m-, p-chlorotoluene; ethers, e.g. diethyl ether, ethyl propyl ether, n-butyl ethyl ether, di-n-butyl ether, diisobutyl ether, diisoamyl ether, diisopropyl ether, cyclohexyl methyl ether, ethylene glycol dimethyl ether, tetrahydrofuran, dioxane; aliphatic or cycloaliphatic hydrocarbons for example heptane, nonane, naphtha fractions within the boiling point range from 70° to 190° C., cyclohexane, methylcyclohexane, Decalin, petroleum ether, hexane, ligroin, 2,2,4-trimethylpentane, 2,2,3-trimethylpentane, 2,3,3-trimethylpentane, octane; and corresponding mixtures. The solvent is used in an amount of from 50 to 10000% by weight, preferably from 100 to 1000% by weight, based on starting material II. It is expedient for the solvent chosen to be such that the boiling point of the solvent agrees with the reaction temperature.

The reaction of the first stage is advantageously carried out in the presence of an acid catalyst. The amount of catalyst can vary from 0.001 to 0.2, in particular from 0.01 to 0.15, equivalent per mole of starting material II. It is also possible to use inorganic or organic acids; in place of monobasic acids it is also possible to use equivalent amounts of polybasic acids. Owing to the problem-free workup, acid ion exchanger resins are particularly suitable, since on completion of the reaction they only need to be filtered off. The acid ion exchanger resins can then be reused without loss of yield.

Suitable acids are for example the following: hydrogen chloride, hydrogen bromide, perchloric acid, sulfuric acid, phosphoric acid, nitric acid, sulfonic acids such as benzenesulfonic and p-toluenesulfonic acids; tetrafluoroboric acid, aliphatic carboxylic acids, such as formic acid, chloroacetic acid, dichloroacetic acid, trichloroacetic acid; acid ion exchanger resins; or corresponding mixtures. The acids can be used in concentrated form, or in mixtures with one another and/or with a solvent, in particular water. Preference is given to acid ion exchanger resins, e.g. Duolite ® C 265, Lewasorb ® AC 10, Lewatit ® SPC 118.

To carry out the reaction of the first stage, a mixture of solvent, acid and compound of the general formula III is brought to the reaction temperature. At this temperature the compound of the general formula II, possibly dissolved in the same or some other solvent, is added dropwise in the course of from 0.1 to 5 hours, which is followed by stirring without cooling for from 0.5 to 25 hours. The water which is freed in the course of the reaction does not interfere with the reaction, but can also be removed by azeotropic distillation. The workup is carried out in a conventional manner, for example by distillation and/or crystallization.

The compound of the general formula IV can also be used without isolation for the 2nd stage, namely the hydrogenating cleavage.

To avoid polymerization losses it is expedient to carry out the reaction in the presence of small amounts of customary polymerization inhibitors, e.g. hydroquinone, hydroquinone monomethyl ether or phenothiazine.

The reaction of the 2nd stage, the hydrogenating cleavage, is effected by heating the compound of the general formula IV in a solvent which is inert in the reaction at 100°–300° C., preferably 130°–200° C., particularly preferably 150°–180° C., in the presence of hydrogen and customary hydrogenation catalysts. The reaction is carried out under a pressure of from 1 to 300 bar, preferably at from 10 to 200 bar, particularly preferably at from 30 to 100 bar, and is complete after from 1 to 50 hours. The workup is effected in a conventional manner, for example by filtering off the catalyst and distilling and/or crystallizing the residue. The starting compound of the general formula III which is freed in the course of the reaction can be reused.

Suitable reactors are for example simply steel autoclaves. The reaction can be carried out batchwise or continuously.

Any customary hydrogenation catalyst is suitable for the reaction of stage 2, examples being Raney nickel, Raney cobalt or even noble metal catalysts such as palladium on carbon, and platinum on carbon. The catalyst is used in the batchwise process in amounts of from 5 to 50% by weight, preferably from 10 to 30% by weight, based on the amount of compound IV used.

Particularly suitable intermediates of the general formula IV are those which are prepared from the preferred starting compounds of the general formulae II and III.

The solvent for the reaction of stage 2 can be any solvent which is inert under the reaction conditions; preference is given to alkanols and cycloalkanols such as ethanol, methanol, n-butanol, isobutanol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethyl butanol, nonyl alcohol, methylcyclohexanol, in particular those of from 1 to carbon atoms.

The overall reaction II+III→IV→I can preferably be carried out with isolation of the intermediate of the general formula IV, but such an isolation is not always necessary.

The 1,3-di(alkoxycarbonylamino)propanes of the general formula I which are preparable according to the invention are for example valuable starting materials for preparing substituted propane-1,3-diamines, which are otherwise in some instances very difficult to obtain. The diamines can be prepared from the 1,3-diurethanes in a simple and conventional manner, for example by alkaline hydrolysis. The 1,3-diurethanes also offer access to 2-oxohexahydropyrimidines, (cf. No. DE-A-1,238,921), which can be used as intermediates for pharmacologically active compounds; cf. J. Amer. Chem. Soc. 79 (1957), 3786–3788.

The 1,3-diurethanes of the general formula I can also be used as starting materials for 1,3-propane diisocyanates.

The Examples below serve to illustrate the invention in more detail.

EXAMPLE 1

(a) 35 g of methacrolein are added dropwise at 60°–65° C. to a mixture of 133.5 g of ethyl carbamate, 30 g of acid ion exchanger resin (Duolite C 265), 0.4 g of hydroquinone monomethyl ether and 400 ml of chloroform in the course of 40 minutes. The mixture is left at that temperature for 1 hour, the ion exchanger is filtered off, the chloroform is distilled off, and the residue is crystallized from ethyl acetate/petroleum ether. This gives 97 g of 2-methyl-1,1,3-tri(ethoxycarbonylamino)-propane (60.8% yield, based on starting methacrolein) having a melting point of 138°–140° C.

(b) 10 g of the 2-methyl-1,1,3-tri(ethoxycarbonylamino)propane obtained in stage 1a) are dissolved in 90 ml of ethanol, 3 g of Raney nickel are added, and hydrogenation is carried out in a stirred autoclave at 165° C. and 50 bar of hydrogen for 10 hours. Conversion is complete, giving 2-methyl-1,3-di(ethoxycarbonylamino)propane with a selectivity of 95%.

Alternative method for the second stage, using palladium on active carbon as hydrogenation catalyst:

10 g of the 2-methyl-1,1,3-tri(ethoxycarbonylamino)-propane obtained in stage a) are dissolved in 90 ml of ethanol, 3 g of palladium on active carbon (10% Pd) are added, and hydrogenation is carried out in a stirred autoclave at 165° C. and 100 bar of hydrogen for 15 hours. Complete conversion gives 2-methyl-1,3-di(ethoxycarbonylamino)propane with a selectivity of 96%.

EXAMPLE 2

(a) 84 g of ethylacrolein are added dropwise at from 60° to 68° C. to a mixture of 267 g of ethyl carbamate, 30 g of acid ion exchanger resin (Duolite C 265), 0.8 g of hydroquinone monomethyl ether and 400 ml of chloroform in the course of 20 minutes. After 60 minutes the catalyst is filtered off, the chloroform is distilled off and the residue is crystallized from ethyl acetate/petroleum ether. This gives 207 g (62.3% yield, based on starting ethylacrolein) of 2-ethyl-1,1,3-tri(ethoxycarbonylamino)propane having a melting point of 120°–122° C.

(b) 130 g of the 2-ethyl-1,1,3-tri(ethoxycarbonylamino)propane prepared in stage (a) are dissolved in 1300 ml of ethanol, 30 g of Raney nickel are added, and hydrogenation is carried out at 200 bar of hydrogen and 165° C. for 15 hours. Removal of the catalyst by filtration and of the solvent and ethyl carbamate by distillation leaves 90 g of 2-ethyl-1,3-di(ethoxycarbonylamino)propane having a purity of 94% (88% isolated yield).

EXAMPLE 3

(a) 35 g of crotonaldehyde are added dropwise at 60°–83° C. to a mixture of 133.5 g of ethyl carbamate, 15 g of acid ion exchanger resin (Duolite C 265), 0.2 g of hydroquinone monomethyl ether and 200 ml of trichloroethylene in the course of 20 minutes, and the mixture is thereafter left at 80° C. for 30 minutes. The catalyst is filtered off, the solvent is distilled off and the residue is crystallized from ethyl acetate/petroleum ether. This gives 83 g (52% yield, based on starting crotonaldehyde) of 3-methyl-1,1,3-tri(ethoxycarbonylamino)propane having a melting point of 103°–105° C.

(b) 10 g of the 3-methyl-1,1,3-tri(ethoxycarbonylamino)propane prepared in Example 3a are hydrogenated at 165° C. and 200 bar of hydrogen in a stirred autoclave with 3 g of Raney nickel and 100 ml of ethanol in the course of 15 hours. Complete converion gives 1-methyl-1,3-di(ethoxycarbonylamino)propane with a selectivity of 96%.

We claim:

1. A process for preparing 1,3-di(alkoxycarbonylamino)propanes of the general formula I

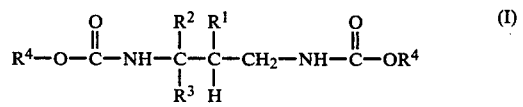

where $R^1$, $R^2$ and $R^3$ can be identical or different and each is hydrogen, or an aliphatic, cycloaliphatic, araliphatic or aromatic radical, and $R^4$ is an aliphatic cycloaliphatic or araliphatic radical, by reacting an $\alpha,\beta$-unsaturated aldehyde with a carbamic acid ester, which comprises reacting in a first stage as the $\alpha,\beta$-unsaturated aldehyde a compound of the general formula II

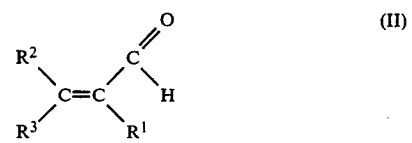

where R¹, R² and R³ have the abovementioned meanings, with a carbamic acid ester of the general formula III $$H_2N-\overset{\overset{O}{\|}}{C}-OR^4 \quad (III)$$

where R⁴ has the abovementioned meanings, at 0°–150° C. to give a 1,1,3-tri(alkoxycarbonylamino)propane of the general formula IV

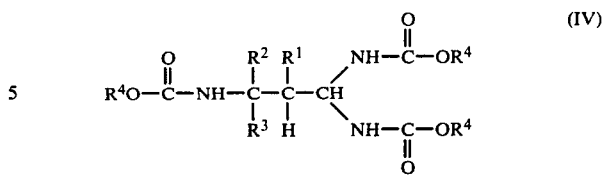

where R¹, R², R³ and R⁴ have the abovementioned meanings, and in a second stage heating the compound of the general formula (IV) in the presence of a hydrogenation catalyst and hydrogen under 1–300 bar at 100°–300° C.

2. The process of claim 1, wherein the first stage is carried out in the presence of an acid catalyst.

3. The process of claim 1, wherein the first stage is carried out at 20°–120° C. and the second stage at 130°–200° C./10 to 200 bar.

4. The process of claim 1, wherein the hydrogenation catalyst used is Raney nickel or palladium on active carbon.

5. The process of claim 1, wherein the first stage is carried out in the presence of a polymerization inhibitor.

6. The process of claim 2, wherein the acid catalyst is an acid ion exchange resin.

* * * * *